United States Patent [19]

Woodruff

[11] 4,316,381
[45] Feb. 23, 1982

[54] MODULATED DETECTOR

[75] Inventor: Terry A. Woodruff, Newark, Del.

[73] Assignee: Hewlett-Packard Company, Palo Alto, Calif.

[21] Appl. No.: 167,856

[22] Filed: Jul. 14, 1980

[51] Int. Cl.³ .................... G01N 27/18; G01N 27/16
[52] U.S. Cl. ..................................... 73/27 R; 422/54
[58] Field of Search ........... 73/27 R, 23.1, 23, 864.81, 73/864.83; 422/54, 89, 95, 98; 23/232 E

[56] References Cited

U.S. PATENT DOCUMENTS

| | | | |
|---|---|---|---|
| 2,255,551 | 9/1941 | Willenborg | 73/27 R |
| 3,790,348 | 2/1974 | Bossart et al. | 422/54 |
| 4,185,490 | 1/1980 | Clouser et al. | 73/23.1 |
| 4,254,654 | 3/1981 | Clouser et al. | 73/27 R |

Primary Examiner—Stephen A. Kreitman
Attorney, Agent, or Firm—Donald N. Timbie

[57] ABSTRACT

The continuous flow of sample fluid, e.g., the elution from the column of a chromatograph, is modulated with the aid of a storage volume such that the flow of sample fluid into the fluid input of a detector varies between maximum and minimum values at a given frequency, the flow of reference fluid to the fluid input of the detector is modulated out of phase, and the differences in output of the detector resulting from these modulated flows is derived by a synchronous detector or demodulator.

10 Claims, 11 Drawing Figures

PRIOR ART

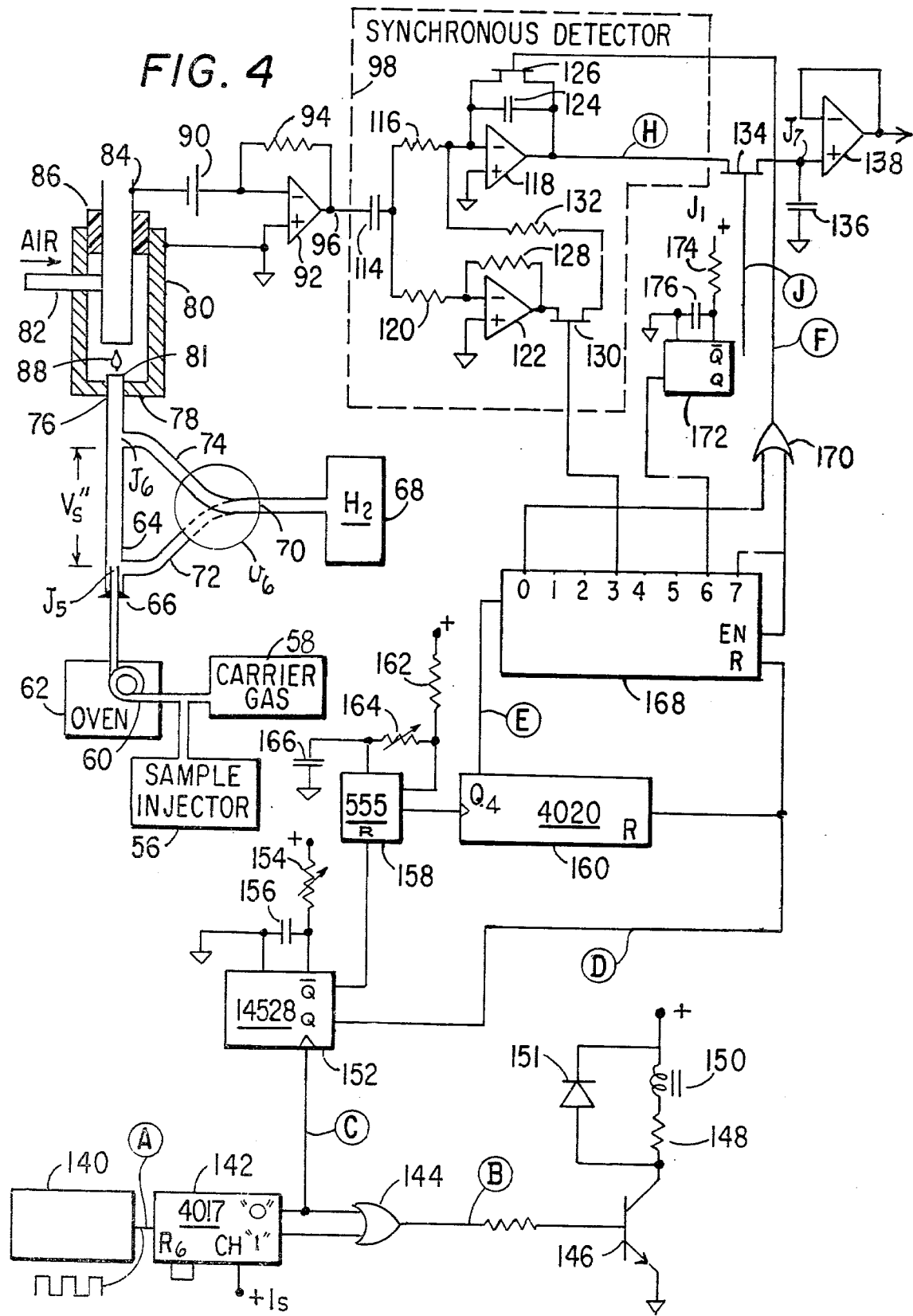

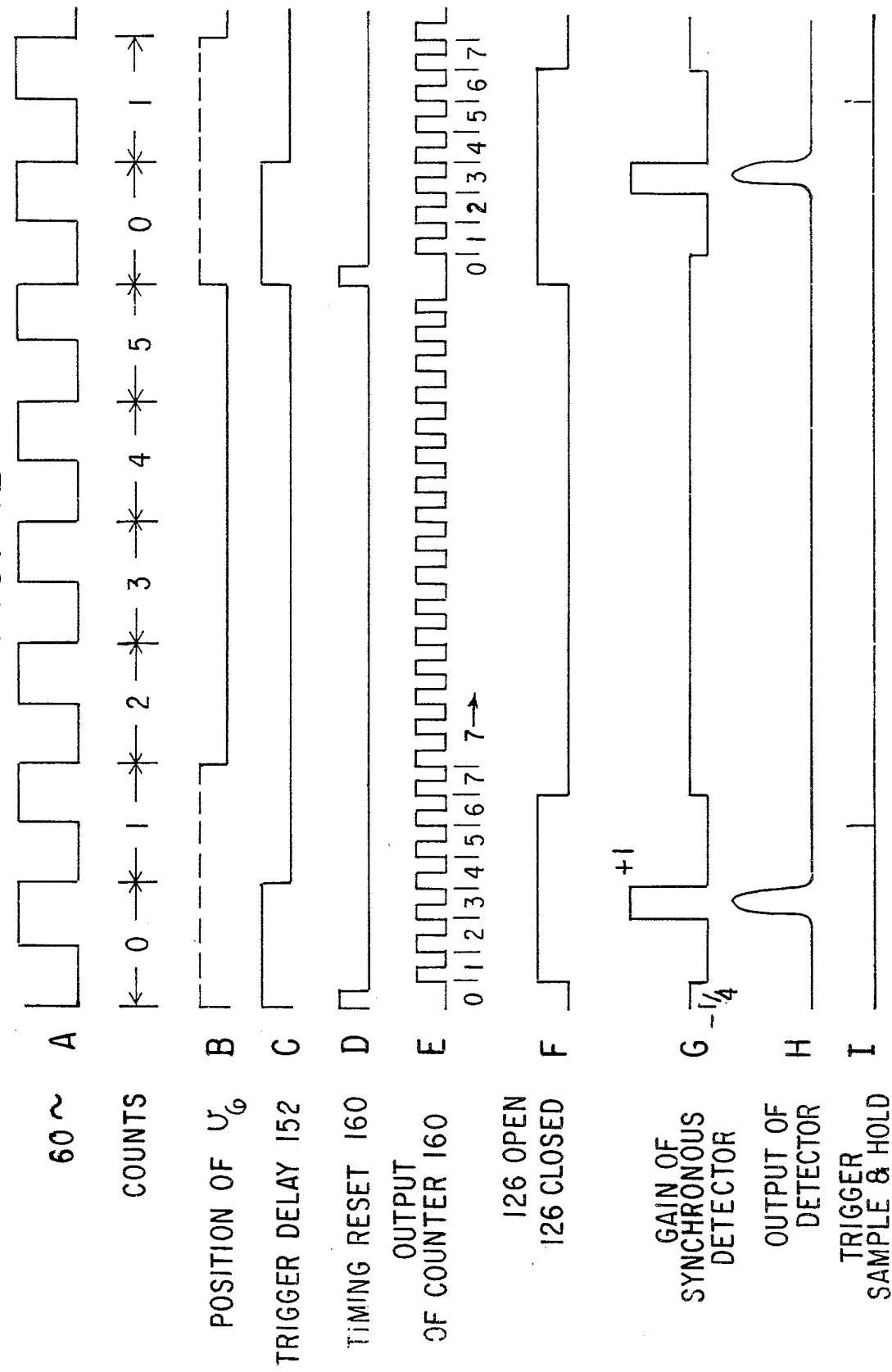

MODULATED DETECTOR

BACKGROUND OF THE INVENTION

This invention relates to improved apparatus for conducting a stream of sample fluid to a detector that responds to a given characteristic of the sample fluid. Although it has application to many instruments, the invention has been found to be of considerable advantage when used with chromatographs which are used to measure the respective quantities of chemicals that are contained in a sample mixture. Basically, a chromatograph is comprised of a sample injector, a column, a detector, and it generally includes an output device or recorder and an integrator. The sample to be analyzed is injected by the injector into a stream of carrier fluid just as it enters the column and, ideally, each chemical contained in the sample is separated from the others so that they respectively elute from the other end of the column at different times. The elutants from the column flow through a detector that outputs an electrical signal corresponding to the value of a given characteristic of the fluid applied to it. For example, in a thermal conductivity cell, TC, the characteristic is the thermal conductivity of the sample gases; in a flame photometric detector, the characteristic is light emissions from sulphur molecules; and in a flame ionization detector, FID, the characteristic is the rate at which ions are produced as the gaseous chemical sample burns in the flame. When the carrier fluid passing through the detector contains no sample chemical, the detector output signal has a baseline value that may be offset from zero, but as separated sample chemicals pass through the detector, the value of the output signal changes so as to form a peak corresponding to the intensity of the characteristic of the sample chemical to which the detector is responsive. The greater the amount of the sample chemical, the larger is the peak. The integrator measures the area of the peak, i.e., the difference between each peak and the continuous baseline value, so as to give a measure of the amount of sample chemical present.

There are three types of noise generally present in the detector signal: low frequency wander and drift in the baseline value; higher frequency variations in the baseline value; and fluctuations in the baseline value that occur so many times during a peak that their net effect on the signal at the output of the integrator is virtually zero.

The effect of the low frequency wander and drift of the baseline can be virtually eliminated from the detector signal by alternately connecting the input of the detector to the column and a source of reference gas, and synchronously detecting or demodulating the output signal of the detector as suggested by John S. Craven and David E. Clouser in their U.S. patent application, Ser. No. 730,559, filed on Oct. 7, 1976, and entitled "Modulated Fluid Detector", now U.S. Pat. No. 4,254,654. If need be, make-up fluid that is the same as or similar to carrier fluid or reference gas as far as detector response is concerned may be added to the elutants from the column so as to increase their flow. While reference gas is flowing to the detector, the column elutant is vented to the atmosphere. During each cycle of alternation, the output signal of the detector varies from one peak value that occurs when the ratio of the concentration of sample gas to the concentration of reference gas contained within the detector is maximum to another peak value when the ratio is a minimum. The synchronous detector outputs a signal related to the difference in the detector signal resulting from the alternating flows of sample and reference gas.

In order to provide sufficient resolution, the frequency of the alternation at which the peak values of the electrical signal occur is chosen to be well above the highest frequency component of the peaks of sample chemical contained in the sample fluid eluting from the column. Inasmuch as this frequency of alternation is fast with respect to slow variation in the baseline value, adjacent peak values of the electrical signal produced by the detector are equally affected by slow variations in the baseline value so that when synchronous detection techniques are used, the effects of the slow variations of the baseline value are virtually eliminated by subtraction. The output signal of the synchronous detector may then be integrated so as to determine the amount of sample chemical corresponding to the peak of sample chemical. Unfortunately, however, because the sample fluid from the column is vented to the atmosphere during half of each cycle of alternation, the energy of the output signal of the detector in response to the sample chemical contained in the sample fluid is half what it would be if the elutant were allowed to flow through the detector continuously, but the noise energy due to the higher frequency baseline variations is the same so that the detector output-to-noise ratio is less than it might ideally be.

BRIEF DESCRIPTION OF THE INVENTION

In accordance with this invention, the signal-to-noise ratio of the signal derived from the detector is improved and the effects of slow variations in the baseline value of the detector are virtually eliminated by modulating the flow of the sample fluid to the detector with the aid of a storage volume so that the flow of sample fluid has a minimum value during first spaced periods of time and a maximum value during second periods of time that are interleaved with the first. The flow of reference fluid to the detector is also modulated, but out of phase so that it has a maximum value during the first periods of time and a minimum value during the second periods of time. Synchronous demodulation of the output signal of the detector virtually eliminates the effects of any low frequency drift. The fact that all of the sample fluid flows through the detector rather than being wasted by venting it to the atmosphere as in the patent application referred to increases the response of the detector to chemicals of interest contained in the flow of sample fluid so as to thereby increase the signal-to-noise ratio. With detectors that respond to the concentration of sample chemicals applied to them, this is the source of the improvement in the signal-to-noise ratio, but with detectors that respond to the rate at which the sample chemicals flow through them, an additional improvement in the signal-to-noise ratio can be effected by modulating the flow of sample fluid so that its minimum flow lasts longer than its maximum flow, i.e., the first periods are longer than the second periods. This makes it possible for the synchronous demodulator to operate in response to the entire energy contributed by the sample chemical to the detector output signal during the second periods when a sample chemical is flowing through the detector at the maximum rate and to only part of the noise energy in the detector output signal occurring during the longer first periods so that the noise energy of the faster variations in baseline value are reduced.

In applying the invention to a detector that is not sensitive to mass flow, such as a TC detector, which provides a signal proportional to the concentration of sample gas within it, a two-to-one signal-to-noise ratio improvement can be effected over that achieved by Craven and Clouser because, instead of disposing of the sample gas eluting from the column during the half-cycle when the carrier gas is flowing through the detector, the sample gas is stored in a storage volume and sent into the detector during the next half-cycle. The signal-to-noise improvement results from the fact that the concentration of sample gas is doubled so as to double the energy of the signal output of the detector while the amount of noise remains the same. Even better results can be obtained with detectors that are non-linear, e.g., in a flame photometric detector, the response is proportional to the concentration squared, so a much greater improvement in signal-to-noise can be obtained.

When, however, the invention is applied to a detector that is sensitive to mass flow rate, such as a flame ionization detector, FID, the signal-to-noise ratio can be further increased because the sample fluid from the column can be stored for a longer first period and then forced through the detector during a much shorter second period so as to produce spaced output pulses having the same energy as would be produced by a continuous flow. The added improvement in signal-to-noise ratio results from the fact that synchronous detection of the spaced pulses can be accomplished in response to the pulses and only a portion of the energy of the remainder of the detector output signal so that the signal energy remains the same while the noise energy is reduced.

DESCRIPTION OF THE DRAWINGS

FIG. 4 illustrates one way of utilizing an FID detector in accordance with this invention;

FIG. 4D includes a series of graphs that are used in explaining the operation of the logic circuits of FIG. 4.

In FIG. 1, which is a schematic and simplified version of the prior art as set forth in the above-identified patent application, an end of a chromatographic column 2 is inserted in one end of a tube 4 and sealed in communication therewith by ferrules 6. As is well known, the sample fluid from the column 2 is a stream of carrier gas containing spaced concentrations of sample gas. The other end of the tube 4 is a vent 5 to the atmosphere. Make-up gas, which also serves as reference gas and which may be the same as the carrier gas, is supplied by a source 8 and is conducted via a tube 10 to a point in the tube 4 that is preferably below the end of the column 2. Reference gas is also conducted via a tube 12 to the fluid input 14 in a cell 16 of a thermal conductivity detector. The make-up gas is added so that the sum of the column and make-up flow is sufficient to sweep the cell 16 during the alloted time. The fluid input 14 is connected by a tube 18 to a point in the tube 4 that is between the junction of the tubes 4 and 10 and the vent 5. The various dimensions have been exaggerated and the schematic has been slightly altered from that of the prior art in the interest of simplicity. A value $v_1$, mounted inside the tube 4, is hinged so as to permit gas from the column 2 to flow out of the vent 5 and prevent it from entering the tube 18 when in the solid-line position and so as to direct gas from the column 2 into the tube 18 and prevent it from going out the vent 5 when in the dotted-line position. A valve $v_2$ is hinged within the tube 12 so as to block the tube 12 when in the dotted-line position and to permit gas to pass through the tube 12 when in the solid-line position. Both valves $v_1$ and $v_2$ are respectively operated so as to be in their dotted-line positions or in their solid-line positions by mechanical coupling that is schematically indicated by the dashed lines 20 and 22. The coupling can be operated by a valve drive circuit 23 which may convert electrical signals into mechanical movement of the couplings 20 and 22 with a solenoid, not shown.

Figure 1:
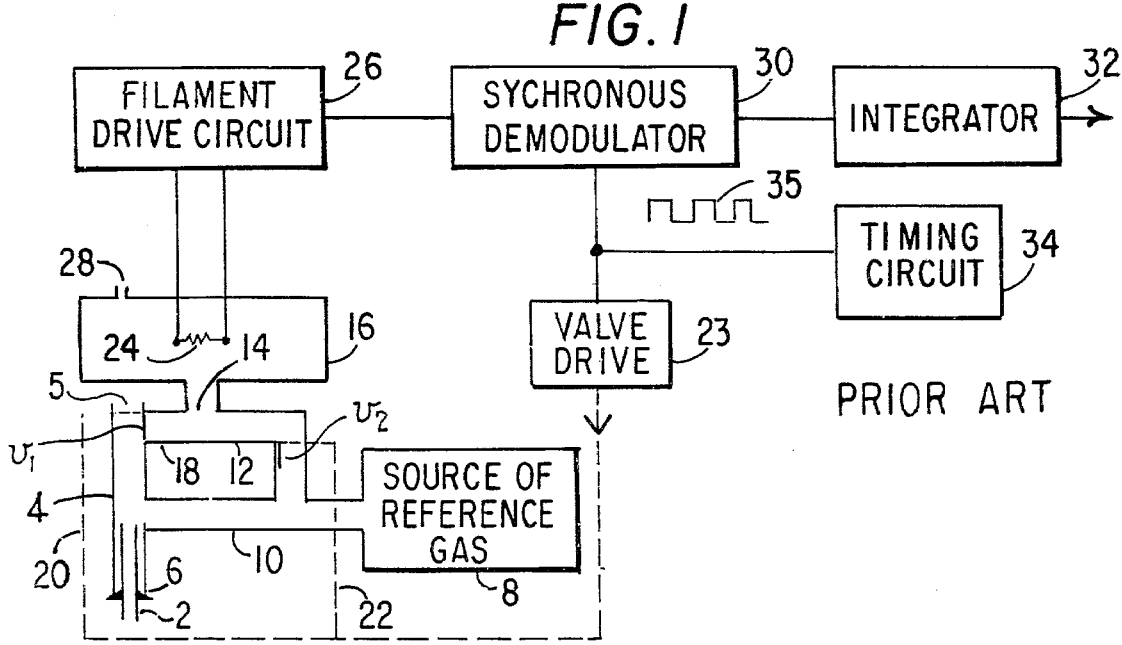
FIG. 1 is a schematic illustration of a system of the prior art utilizing a thermal conductivity detector.

As is customary, a filament 24 that is contained in the thermal conductivity cell 16 is kept at a constant temperature by a filament drive circuit 26. Gases entering the fluid input 14 pass over the filament 24 and exit at a vent 28. The voltage applied to the filament 24 by the filament drive circuit 26 in order to maintain it at a constant temperature is the detector output signal and corresponds to the thermal conductivity of the gases within the cell 16. This output signal is applied to a synchronous detector 30, and its output is applied to an integrator 32. A timing circuit 34 provides a square wave 35 of voltage so as to operate the synchronous detector 30 and the valve drive circuit 23 in synchronism. Delays which may be required have been omitted from the drawing in the interest of simplicity. During one half-cycle of the square wave 35, the values $v_1$ and $v_2$ are in their dotted-line positions; during the next half-cycle, the valves $v_1$ and $v_2$ are in their solid-line positions.

The operation of the prior art detector system of FIG. 1 will now be explained by reference to the graphs of FIGS. 1A and 1B in which a dash-dot line 36 represents the flow of sample fluid from the column 2, the peak 38 represents the portion of the sample fluid flow 36 that is the sample chemical being analyzed, and the line 40 represents the sum of the sample fluid flow from the column 2 and the flow of make-up or reference gas that is added to it via the tube 10. During the half-cycles v, when the valves $v_1$ and $v_2$ are in their solid-line positions, reference gas flows through the cell 16; and during the half-cycles d, when the valves $v_1$ and $v_2$ are in their dotted-line positions, sample chemical gas indicated by the cross-hatched area under the peak 38, carrier gas indicated by the area between the peak 38 and the line 36, and make-up gas (herein shown as being reference gas) indicated by the area between the lines 36 and 40 flow through the cell 16. Thus, samples of the peak 38 of sample chemical that are indicated by the cross-hatched area under the peak 38 are applied to the fluid input 14 of the cell 16 during the half-cycles d. In order to preserve the shape of the peak 38, these samples must occur at a frequency that is more than twice the highest frequency of interest in a peak so that a number of samples occur during each peak of sample chemical. As previously pointed out, the sample fluid flow 36 is often insufficient for the sample fluid to pass entirely through the cell 16 during a half-cycle d and the flow is increased by addition of make-up gas, herein shown as being reference gas, via the tube 10. This, of course, reduces the concentration of the sample chemical 38 by a factor equal to the value of the sample fluid flow 36 divided by the value of the flow 40. This does not represent a reduction in concentration in comparison with prior art systems in which the sample fluid flow is continuous and not modulated because make-up gas has to be added in such systems as well in order that the peaks can be resolved. It does, however, represent a loss in signal energy owing to the fact that half of the sample chemical is wasted by being passed through the vent 5.

Figure 1A:
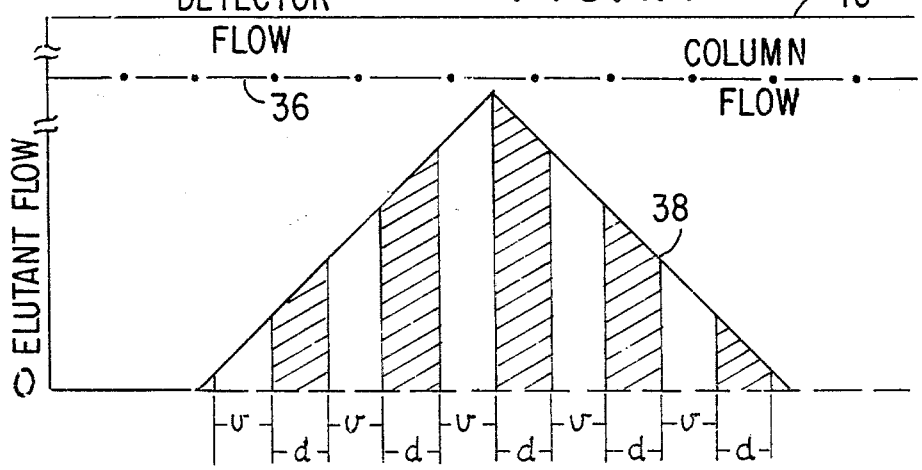
FIG. 1A includes graphs of fluid flow used in explaining the operation of FIG. 1 as well as the operation of FIG. 2.
Figure 1B:
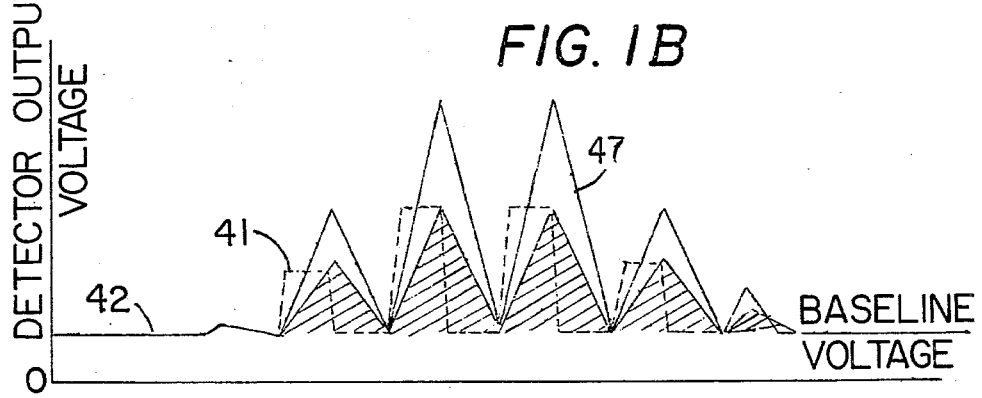
FIG. 1B includes graphs representing a TC detector output signal used in explaining the operation of FIGS. 1 and 2.

The carrier gas contained in the sample fluid emerging from the column 2 and the reference gas are assumed to have the same thermal conductivity so that during their presence in the cell 16, the output voltage of the filament drive circuit 26 has a value known as the baseline value 42 indicated in the graph of detector output voltage shown in FIG. 1B. These gases are generally selected so as to have a thermal conductivity that is much less than that of any sample chemical to be analyzed so that when sample chemicals are passing through the cell 16, the output voltage of the filament drive circuit increases as indicated by the cross-hatched triangular pulses of FIG. 1B. Their sloping sides reflkct the fact that the concentration of sample chemical in the cell 16 gradually increases as the chemical enters the cell during the periods d and gradually decreases as the chemical leaves the cell during respectively subsequent periods v. The triangular shape of the pulses indicate that the combination of the flow rate 40 and the volume of the cell 16 is such that the first part of a sample chemical to enter leaves the cell 16 as the last part of the sample chemical enters it. With a smaller volume or faster flow, the pulses would be trapezoidal as indicated by the dashed line 41, the flat tops indicating that the cell 16 contains sample chemical for some time.

In ways known to those skilled in the art, the synchronous detector or demodulator 30 will output a signal related to the difference in the detector signal resulting from the alternating flows of sample and reference gas through the cell 16 so as to eliminate the effect of any low frequency variation in the value of the baseline 42, if such were present. It will be noted, however, that there is no discrimination against noise near the modulation frequency because it is present during all the periods v and d.

Figure 2:
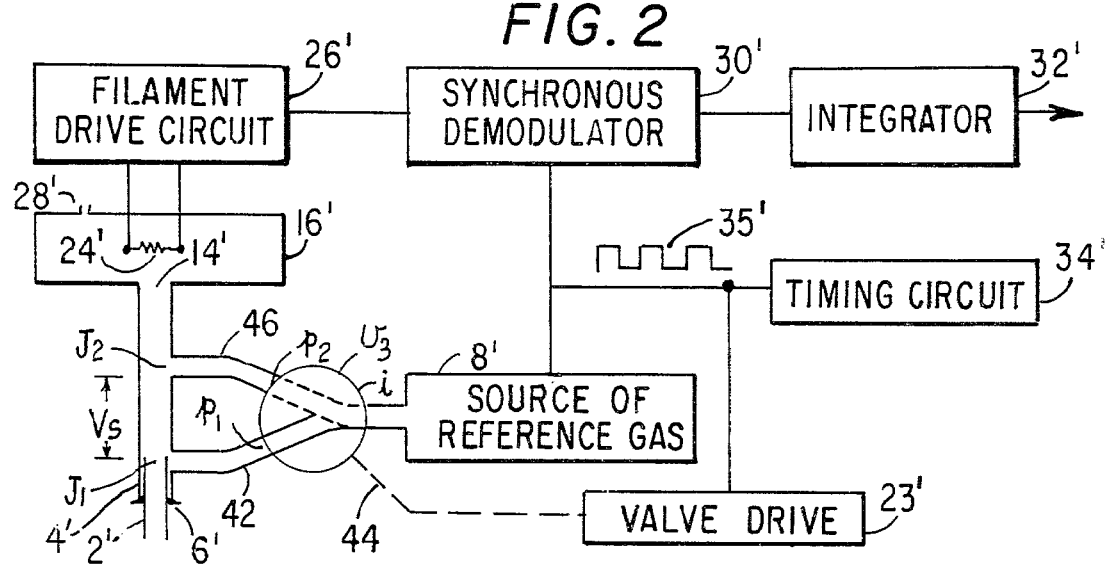
FIG. 2 is a schematic illustration of a thermal conductivity detector system in which the flows of sample and reference gas are modulated by one type of apparatus in accordance with this invention.

Reference is now made to FIG. 2 which shows one way of incorporating the sample fluid modulation system of this invention in a thermal conductivity detection system such as shown in FIG. 1. Components of FIG. 2 that are substantially the same as those of FIG. 1 are indicated by the same numerals primed and are not further described. It will be noted that the length of the tube 4' between the end of the column 2' and the fluid input 14' is greater than in FIG. 1 so as to form a storage volume $V_S$ and that there is no vent corresponding to the vent 5 so that all of the sample fluid, in this case sample gas, from the column 2' will, as will be described, eventually pass through the fluid input 14' instead of half of it being wasted.

Modulation of the flow of sample gas, which includes carrier gas and sample chemicals in gaseous from that elute from the column 2', to the fluid input 14' of the cell 16' of the detector may be achieved by the following apparatus. The cross-section of the tube 4' proximate the end of the column 2' is a first input port $J_1$ coupled to the column 2' so as to receive the entire flow of sample fluid. One end of a tube 42 is connected so as to be in communication with the first input port $J_1$ and its other end is connected to one output $p_1$ of a valve $v_3$, the input i of the valve being coupled to receive reference gas from the pressurized source 8'.

During a first polarity of the wave 35', which is not necessarily a square wave, the input i of the valve $v_3$ is not connected to the output port $p_1$ because of the position, now shown, of the mechanical connection 44 between the valve $v_3$ and the valve drive circuit 23', so that sample fluid 36 flows into the storage volume $V_S$ and then to the fluid input 14' at the rate R at which it elutes from the column 2'. The flow of sample fluid to the fluid input 14' is therefore at a minimum value. During the next or second half-cycle of the wave 35', the valve drive circuit 23' changes the position of the mechanical coupling 44 so that the valve $v_3$, which may be a Clippard EVO-3, connects its output port $p_1$ with its input i so that reference gas sweeps the stored sample fluid from the storage volume $V_S$ through the fluid input 14' of the detector cell 16' with a maximum flow.

Modulation of the flow of reference fluid to said fluid input 14' of said detector is accomplished by the following apparatus. The opening $J_2$ at which one end of a tube 46 intersects the tube 4' is a second input port and is coupled to the fluid input 14' of the detector cell 16'. The other end of the tube 46 is coupled to an output $p_2$ of the valve $v_3$. During the second polarity of the wave 35' previously referred to, the valve $v_3$ is positioned in its dotted-line position by the valve drive circuit 23' and the mechanical linkage 44 so that its output port $p_2$ is connected to its input i thereby maximizing the flow of reference gas to the fluid input 14' of the detector cell 16'. During the first polarity of the wave 35', the valve drive circuit 23' rotates the valve $v_3$ so that its output port $p_2$ is not connected to its input i, thereby minimizing the flow of reference fluid to the fluid input 14'. Thus, the flow of sample fluid from the column 2' to the fluid input 14' and the flow of reference fluid from the source 8' to the fluid input 14' are modulated out of phase with each other. Instead of using one valve $v_3$ to modulate the flows of sample gas and reference gas, it is apparent that two entirely separate valves could be used as long as they are properly synchronized.

The operation of the invented apparatus illustrated in FIG. 2 will now be explained with reference to the graphs of FIGS. 1A and 1B. During the half-cycle of the wave 35' which occurs during the periods d of FIG. 1A, the valve $v_3$ of FIG. 2 is in its solid-line position so that the reference gas applied to the first input port $J_1$ sweeps a slug of gas previously stored through the fluid input 14', thus increasing the detector output voltage.

As the slug leaves the volume $V_S$, it is followed by a mixture of the reference gas entering at $J_1$ and the sample gas from the column $2'$. The flow rates $F_c$ of the sample gas emerging from the column $2'$ and $F_R$ of the reference gas, the volume $V_S$ and the frequency of the wave $35'$ are such that when the last of the slug enters the fluid input $14'$ of the detector cell $16'$, the valve $v_3$ changes to its dotted-line position and stays there during the half-cycle v. Reference gas now enters at $J_2$ and pushes the slug of gas through the cell $16'$, thus decreasing the detector output voltage. During the periods v, the sample gas continues to flow into the storage volume $V_S$ so as to add to the sample gas that followed the slug during the previous period d. Thus, the concentration of the sample chemical in the slug that is swept through the fluid input $14'$ during the periods d can, depending on the ratio of the flows $F_c$ and $F_R$, be up to twice that obtained in FIG. 1 so as to produce the larger pulses 47 of FIG. 1B at the output of the filament drive circuit $26'$. If the flow rates $F_c$ and $F_R$ were relatively close, trapezoidal waves of greater amplitude would be produced. The synchronous detector $30'$ operates to derive a signal related to the peak-to-peak value of the wave 47.

Figure 3:
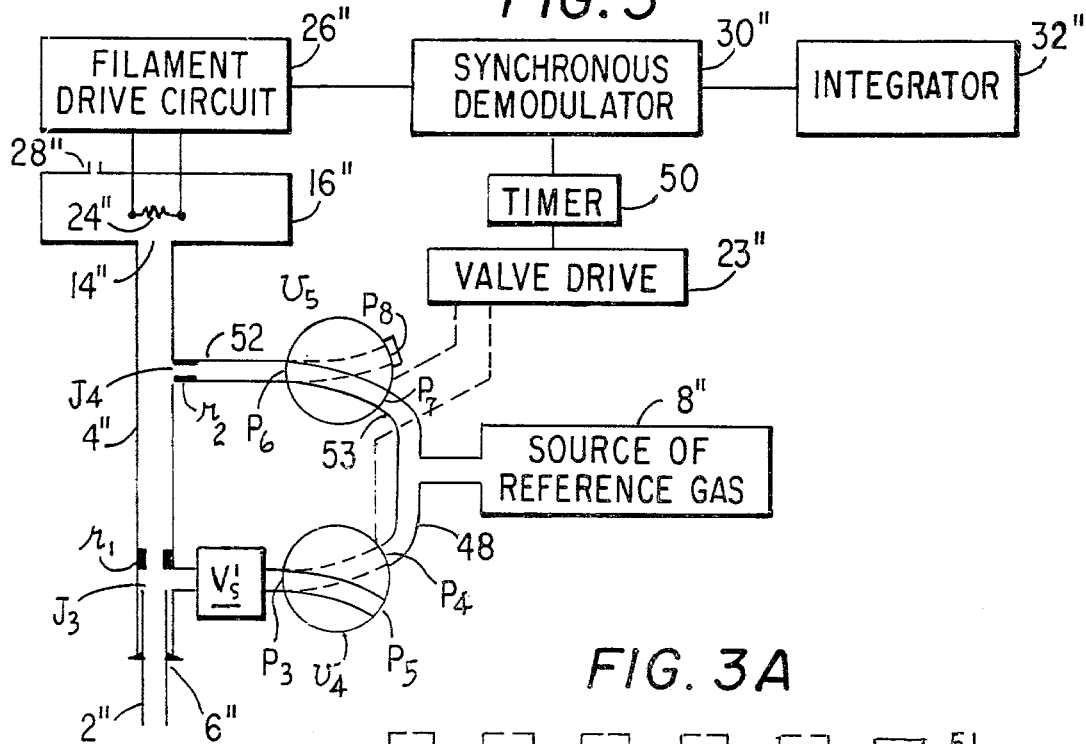
FIG. 3 is a schematic illustration of a thermal conductivity detector system in which the flows of sample and reference gas are modulated by a different type of apparatus in accordance with this invention.

Reference is now made to the embodiment of the invention shown in FIG. 3 wherein components corresponding to those of FIGS. 1 and 2 are indicated by the same numerals with a double prime. Those components used only in FIG. 2 are indicated by the same numerals with a single prime. FIG. 3 is included to show a different way of incorporating the storage volume into a system in accordance with this invention, but it also includes other invention features which will be the subject of another patent application.

Figure 3A:
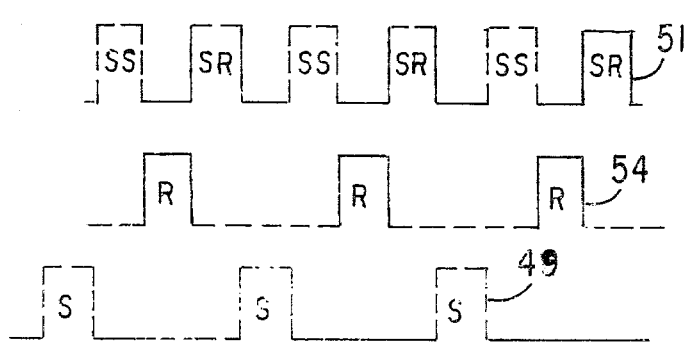
FIG. 3A includes graphs used in explaining the operation of FIG. 3.

Modulation of the flow of sample fluid to the fluid input $14''$ may be accomplished by the following apparatus. A first input port $J_3$ to which sample fluid may be applied is the cross-section of the tube $4''$ surrounding the end of the column $2''$. One end of a storage volume $V_S'$ is connected to the tube $4''$ near the first input port $J_3$, and the other end of the storage volume $V_S'$ is connected to a port $p_3$ of a rotary valve $v_4$ having a port $p_4$ connected via a tube 48 to the pressurized source $8''$ of reference gas and a port $p_5$ in communication with the atmosphere. While in its solid-line position, as indicated by the solid lines of the graph 49 of FIG. 3A, the ports $p_3$ and $p_5$ are in communication and sample fluid flows from the column $2''$ into the storage volume $V_S'$. The presence of a restrictor $r_1$ in the tube $4''$ prevents most of the sample fluid from passing above it. Thus, during this period, the flow of sample fluid to the fluid input $14''$ is at a minimum. During the periods indicated by the dotted pulses S of the wave 49 of FIG. 3A, the valve $v_4$ is in its dotted-line position so that the ports $p_3$ and $p_4$ are in communication, thereby permitting pressurized reference gas to sweep the sample fluid stored in $V_S'$ during the previous period through the restrictor $r_1$ and into the fluid input $14''$. While the valve $v_4$ is in the dotted-line position, the flow of sample fluid to the fluid input $14''$ is at a maximum.

At the end of a pulse S of the graph 49, the sample fluid stored in the storage volume $V_S'$ has entered the cell $16''$ and a timer 50 outputs a dotted pulse SS of a graph 51 to the synchronous demodulator $30''$ causing it to measure the detector output of the filament drive circuit $26''$.

Modulation of the flow of reference gas to the fluid input $14''$ of the detector cell $16''$ is accomplished by the following apparatus. An opening at $J_4$ at which one end of a tube 52 intersects the tube $4''$ is a second input port and is coupled to the fluid input $14''$. The other end of the tube 52 is connected to a port $p_6$ of a valve $v_5$ having a port $p_7$ connected via a tube 53 to the source $8''$ of reference gas and a port $p_8$ which is closed off. When the valve $v_5$ is in its solid-line position, as indicated by the solide line pulses R of a graph 54 of FIG. 3A, the ports $p_6$ and $p_7$ are in communication so that the flow of reference gas to the fluid input $14''$ is a maximum; and when the valve $v_5$ is in its dotted-line position, as also indicated by the dotted portions of the graph 54, the ports $p_6$ and $p_8$ are in communication so that the flow of reference gas to the fluid input $14''$ is a minimum. A restriction $r_2$ in the tube 52 substantially prevents sample fluid from entering the tube 52 when the flow of sample fluid is a maximum and controls the amount of reference flow.

At the end of a pulse R of the graph 54, the reference fluid has entered the cell $16''$, and the timer 50 outputs a solid-line pulse SR shown in the graph 51 to the synchronous demodulator $30''$ causing it to measure the output of the filament drive circuit $26''$. In a manner known to those skilled in the art, the synchronous demodulator $30''$ derives a signal equal to the difference between the response of the filament drive circuit $26''$ to the presence of sample fluid sitting in it during a pulse SS and its response to the presence of reference fluid sitting in it during the next pulse RR.

FIG. 4 illustrates one way of incorporating the modulation of the flow of sample fluid and reference fluid in a system utilizing a detector such as a flame ionization detector that is responsive to the rate at which sample chemicals flow through it. The illustrated system includes an FID detector and the apparatus for modulating the flow of sample gas containing the chemicals to be analyzed, a synchronous detector or demodulator, and logic circuits for controlling the modulation and the synchronous detector.

The flame ionization detector, FID, and the apparatus for modulating the flow through it in accordance with this invention may be described as follows. A sample to be analyzed is injected in gaseous form by a sample injector 56 into a stream of carrier gas from a source 58 as it enters one end of a column 60 that is contained in an oven 62. The other end of the column 60 is inserted in a tube 64, and a gas-tight seal is provided between the exterior of the column 60 and the interior of the tube 64 by ferrules 66. Flammable gas such as hydrogen, which is herein considered to be reference gas, is supplied by a pressurized source 68 to an input 70 of a three-way valve $v_6$ which may be a Clippard EVO-3. When the valve $v_6$ is in its dotted-line position, its input 70 is connected to a tube 72 that communicates with the tube 64 at a point $J_5$ that is preferably slightly below the end of the column 60; and when the valve $v_6$ is in its solid-line position, its input 70 is connected to a tube 74 that communicates with the tube 64 at a point $J_6$. The space in the tube 64 between the points $J_5$ and $J_6$ is a storage volume $V_S''$.

The FID detector may be described as follows. The tube 64 extends beyond the point $J_6$ and through an opening 76 in the center of a metal disc 78 on which a hollow metal cylinder 80 is coaxially mounted. The end 81 of the tube 64 that is within the cylinder 80 is in this illustration the fluid input of the detector. A gas-tight electrically conductive seal is formed in a manner not shown between the exterior of the tube 64 and the edge of the opening 76. A tube 82 that extends through the cylinder 80 at a point remote from the disc 78 provides means for introducing a desired flow of air from a source, not shown, into the interior of the cylinder 80. An ion collector in the form of a hollow metal cylinder 84 that is coaxial with the cylinder 80 extends to a point just above the fluid input 81 and is insulated from the cylinder 80 by an annulus 86 of insulating material that forms a gas-tight seal between the exterior of the cylinder 84 and the interior of the cylinder 80. Air flows from the tube 82 down through the annular space between the cylinders 80 and 84 to the bottom of the collector cylinder 84 and up through it to the atmosphere at its upper end. Hydrogen or other flammable gas that is introduced into the tube 64 at $J_5$ or $J_6$ mixes with the air at the bottom of the collector cylinder 84 so as to form a steady flame 88 when the mixture is ignited.

Modulation of the flow of sample fluid, in this case carrier gas and sample chemicals in gaseous form that elute from the column 60 to the fluid input 81 of the detector, is achieved by the structure described as follows. The cross-section of the tube 64 proximate the end of the column 60 is a first input port coupled to the column 60 so as to receive the entire flow of sample gas emerging therefrom. The valve $v_6$ is positioned in its solid-line position during first periods $P_1$ of a control wave shown in graph A of FIG. 4A in a manner to be described and in its dotted-line position during the second periods $P_2$. During the first periods $P_1$, the input 70 of the valve is not connected to the tube 72 so that sample fluid flows at the slow rate $F_C$ at which it emerges from the column 60 into the storage volume $V_S''$. The flow of sample gas to the fluid input 81 is at a minimum value. During the periods $P_2$, the valve $v_6$ is positioned in a manner to be described in its dotted-line position so that hydrogen sweeps the sample fluid that is stored in the volume $V_S$ into the fluid input 81 with a flow having a maximum value.

Modulation of the flow of reference fluid, herein the flammable gas hydrogen, to the fluid input 81 of the detector is accomplished by the structure described in the following manner. The opening in the tube 64 that communicates with the end of the tube 74 is a second input port and is in communication with the fluid input 81 of the detector. During first periods $P_1$ of the control wave of the graph A of FIG. 4A, the valve $v_6$ is positioned in its solid-line position so that the flow of the reference gas, hydrogen, into the second input port is at a maximum value. During a succeeding periods $P_2$, the valve $v_6$ is positioned in its dotted-line position so that the flow of reference gas alone to the fluid input 81 is at a minimum value. Thus, the modulations of the flows of sample gas and pure reference gas are out of phase with each other.

The output signal of the detector is derived as follows. A battery 90 or other direct current voltage source is connected between the ion collector cylinder 84 and the inverting input of an operational amplifier 92. The cylinder 80 and the non-inverting input of the amplifier 92 are connected to ground, and a resistor 94 is connected between the output 96 of the amplifier 92 and its inverting input. As ions are formed in the flame 88, they are attracted to the collector 84 because of the electrostatic field between it and the tube 64 and cause a detector output voltage to appear at the output 96 that is proportional to the rate at which ions are formed. Thus, if the flow of sample gas from the column 60 through the flame 88 is increased, the absolute value of the voltage at the detector output 96 will be increased. The detector output 96 is connected to synchronous detecting or demodulating means to be described that are contained within a rectangle 98. Control of the switches in the rectangle 98 as well as control of the valve $v_6$ is effected by logic circuits to be described that are located below the rectangle 98.

Figure 4A:
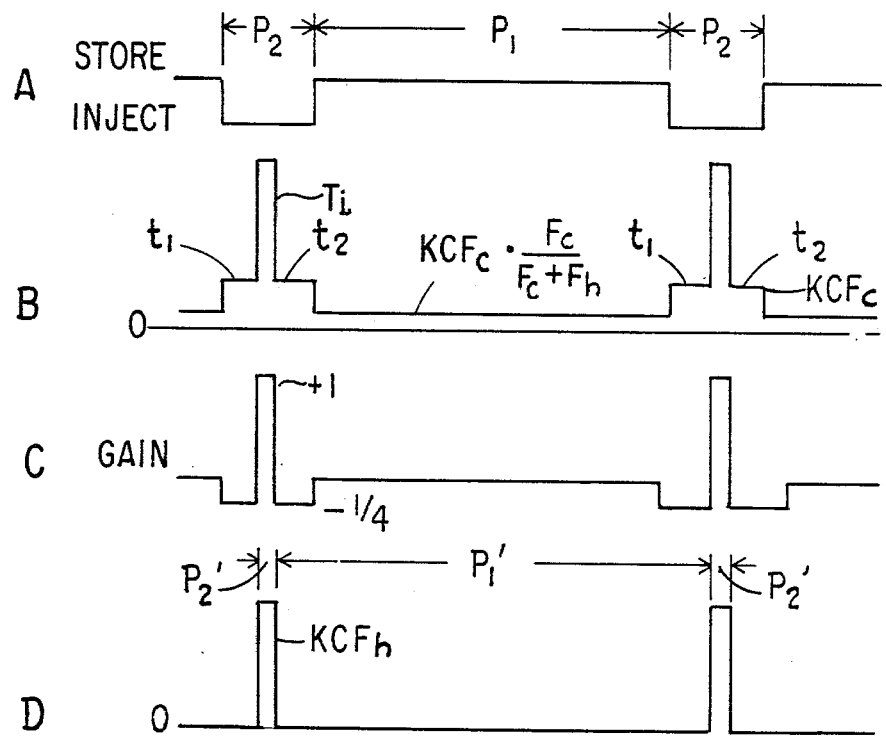
FIG. 4A is a series of graphs used in explaining the overall operation of FIG. 4 as well as the operation of FIG. 4 when the alternative structure of FIG. 4B is used in it.

Before considering the details of the synchronous detector and the logic circuits, however, reference is made to FIG. 4A for a general description of the overall operation of the detector system of FIG. 4. The current produced by the detector includes a baseline component and noise as well as a desired component that is proportional to the product of the concentration c of sample chemicals contained in the sample fluid eluting from the tube 64 and the rate at which they flow through the flame 88. Only the desired component is illustrated in FIG. 4A in which the graph A shows the periods $P_1$ and $P_2$ as previously noted when the valve $v_6$ is respectively in its solid-line and dotted-line positions, a graph B shows the detector output signal at 96, and a graph C shows one variation in the gain of the particular circuit of FIG. 4 that may be used to perform synchronous detection or demodulation.

Assume that sample gas having a concentraction C of sample chemicals is continuously flowing during the periods $P_1$ and $P_2$ at a rate of $F_c$ cm$^3$/sec from the column 60 into the storage volume $V_S''$. During the first periods $P_1$, the valve $v_6$ is in its solid-line position so that hydrogen enters the tube 64 at the junction $J_6$ with a flow of $F_h$ cm$^3$/sec; and during the second periods $P_2$ that are interleaved with the periods $P_1$, the valve $v_6$ is in its dotted-line position so that hydrogen enters the tube 64 at the junction $J_6$ with the same flow of $F_h$ cm$^3$/sec. Thus, sample gas in which sample chemicals have a concentration C is stored in the storage volume $V_S''$ during periods $P_1$ and is swept from the storage volume $V_S''$ and into the flame 88 during periods $P_2$.

Consider the cyclic operation of the FID detector at the transition from period $P_1$ to period $P_2$. Due to the distance between $J_6$ and the flame 88, it takes a time $t_1$, graph B, for the stored sample to reach the flame 88. The current produced by the FID detector during $t_1$ will be subsequently explained. During $T_i$, the stored sample gas with a concentration C is swept through the flame 88 at the sum of the flow rates $F_c$ and $F_h$ so as to produce a current $KC(F_c+F_h)$ wherein K is a proportionately constant. This is the desired signal; it lasts for $P_1F_c/(F_c+F_h)$ seconds.

After all the stored sample gas has flowed through the flame 88, the flow through the flame is comprised of the flow $F_c$ of sample gas from the column 60 and the flow $F_h$ of the hydrogen, but the rate of flow of sample chemicals cannot exceed the rate at which they flow from the column 60 so that the current produced is $KCF_c$. This lasts during the time $t_2$, graph B, i.e., until a period $P_2$ ends and the following storage period $P_1$ begins.

At this time, the concentration of sample chemicals in the storage volume $V_S''$ is a diluted value $CF_c/(F_c+F_h)$. During the period $P_1$, this diluted mixture is swept by the effluent from the column 60 at a flow rate $F_c$ into the flow $F_h$ of hydrogen entering the tube 64 at $J_6$ so as to produce a current $KF_c \cdot CF_c/(F_c+F_h)$. While the diluted sample gas is being swept into the flame 88, the effluent from the column 60 that contains sample gas at the full concentration C is entering $V_S''$, but the volume between $J_6$ and the flame 88 still contains diluted sample gas. Thus, when $P_2$ starts and the flow $F_h$ of hydrogen is conducted by $v_6$ to $J_5$, the diluted sample gas is swept through the flame 88 during $t_1$ at a flow of $F_c+F_h$ so as to produce a current $KCF_c/(F_c+F_h)\cdot(F_c+F_h)$ or $KCF_c$, the same as during the time $t_2$. The cycle is then repeated.

The desirable volume for $V_S''$ is bounded by $V_S''>P_1F_c$ so that the undiluted sample from column 60 does not reach the flame 88 before $P_2$ and thus waste sample gas, and by $V_S''<P_2(F_c+F_h)$ so that $V_S''$ can be swept clear of stored sample gas and not waste it.

If the signal represented by the graph B that appears at the output 96 is integrated with successive gains of $-\frac{1}{4}$ for two units of time, unity for one unit of time, and $-\frac{1}{4}$ for two units of time during the periods $P_2$, the effect of any low frequency change occurring in the baseline value during these five units of time will average zero, but if the period of unity gain is made to coincide with the time $T_i$, the desired signal can be detected without attenuation. As indicated in the graph B, the value of the signal level $KCF_c$ occurring during the five units of time is not the same as when pure hydrogen is flowing through the detector during periods $P_1$ but the difference will be small as the value of $KCF_c$ has been illustrated as being much larger than it really is because $(F_c+F_h)/F_c$ in a practical case is about twenty instead of five, as shown. Those skilled in the art will appreciate that the times of negative gain could also be made to occur at any portion of the periods $P_1$ and could be of different duration as long as the product of the duration of the negative gain and its value equals the gain-time product occurring during $T_i$. Variation of the gain of an integrating amplifier 118 in any such manner accomplishes synchronous detection or demodulation.

Because the product of the negative gain and the time it occurs is less than unity gain for the entire time, $P_1+P_2$, the noise energy is reduced but the signal energy is not reduced so that the signal-to-noise ratio is improved. It is still further improved by the fact that a variation occurring during the five periods that the integrating amplifier 118 is active will have less effect because the integration during periods of negative gain will only partially offset the integration taking place during the one period of unity gain. It would, of course, be possible to utilize any form of synchronous detector that derived the difference between the peak signal occurring during $T_i$ and a sample of the same duration and gain taken during any other time.

To ease switching requirements, it is possible to make $P_2$ substantially longer than the calculated $T_i$, e.g., it can be made as long as about $\frac{1}{2}$ of $P_1$ without significant loss in efficiency that results because sample gas from the column is not contributing to the output signal during the time $t_1$ and $t_2$.

Figure 4B:
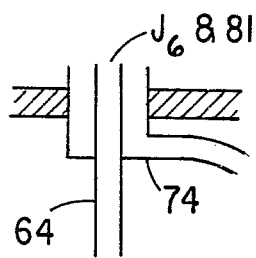
FIG. 4B is an alternative structure for introducing reference gas to the FID detector of FIG. 4.

Rather than joining the tube 74 to the tube 64 at $J_6$ as shown, the tube 74 may terminate adjacent to the end of the tube 64 or may join with a coaxial tube surrounding the tube 64 as indicated in FIG. 4B so as to allow the flame to burn at the exit of either tube 64 or tube 74. Means may be provided to restrict the flow of hydrogen through the tube 74 during portions of the periods $P_1$ during which the gain of the amplifier 118 is zero, so that just enough flow is provided to keep the flame alive and thus conserve hydrogen, or the flow may even be made zero and means provided to reignite the flame for each cycle.

Figure 4C:
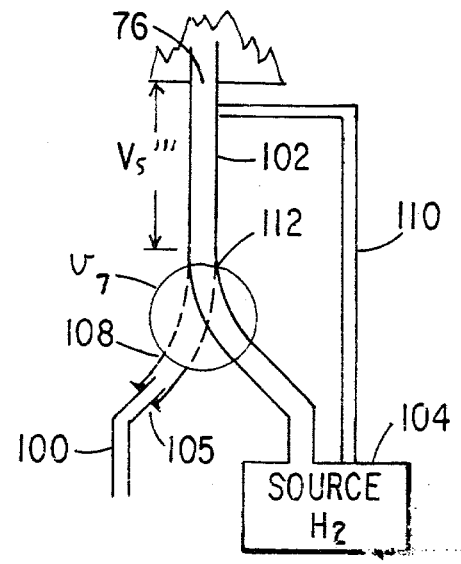
FIG. 4C shows an alternative structure that may be substituted for a part of the structure used in FIG. 4.

One of the advantages of the valving arrangement of FIG. 4 is that the often corrosive sample chemical in the sample gas eluting from the column 60 does not flow through the valve $v_6$, but there is some loss in efficiency unless $P_2$ is made to have the same or only a slightly longer duration than $T_i$ by a relatively precise and expensive implementation. FIG. 4C shows an arrangement which may be substituted for the components associated with the valve $v_6$ of FIG. 4 in which greater efficiency is attained by arranging that a valve $v_7$ alternately pass either sample gas from a column 100 via a tube 102 to the fluid input 81 when in its dotted-line position or flammable gas such as hydrogen from a source 104 when in its solid-line position. Ferrules 105 provide a seal between the outside of the column 100 and the inside of the input 108 of the valve $v_7$ to which the column 100 is connected. A line 110 may be provided to supply a small constant flow of flammable gas so as to prevent the flame 88 from going out while sample gas is being stored. The storage volume $V_S'''$ is the volume of the tube 102 between the output 112 of $v_7$ and the fluid input 81. As shown in graph D of FIG. 4A, the sample gas from the column 100 flows into the volume $V_S'''$ during time $P_1'$ and if $V_S'''>F_cP_1'$, no sample flows through the flame 88 during $P_1'$. During $P_2'$, the sample gas stored in $V_S'''$ is swept through the flame 88 by the flow $F_h$ of hydrogen alone because the column 100 is blocked off. Neither sample gas nor hydrogen is wasted.

Although many circuits may be used to perform the function of synchronous detection or demodulation, the one illustrated in the rectangle 98 of FIG. 4 and now to be described has been found suitable. The output 96 of the FID detector is coupled by a capacitor 114 and a resistor 116 to the inverting input of an integrating operational amplifier 118, and by the capacitor 114 and a resistor 120 to the inverting input of an inverting operational amplifier 122. The non-inverting inputs of amplifiers 118 and 122 are connected to ground. A capacitor 124 and the source-drain path of an FET 126 are connected in parallel between the output of the amplifier 118 and its inverting input; and a resistor 128 is connected between the output of the amplifier 122 and its inverting input. The resistors may all have the same value, e.g., 200K ohms. The source-drain path of an FET 130 and a resistor 132 of 160K ohms are connected in series between the output of the amplifier 122 and the inverting input of the amplifier 118. When the FET 130 is conducting, the relative gain of the integrating amplifier 118 is $-\frac{1}{4}$; and when it is not conducting, the gain of the amplifier 118 is 1. This assumes, of course, that the FET 126 is not conducting.

A sample-and-hold circuit is formed by connecting the source-drain path of an FET 134 between the output of the integrating amplifier 118 and one side of a capacitor 136, the other side being connected to ground. The integrated output signal of the detector system appears at the junction $J_7$ of the FET 134 and the capacitor 136 and may be coupled to other circuits by a buffer amplifier 138.

In the following description of one type of logic system that may be used to operate the FETs 126, 130 and 134, references are made to graphs of FIG. 4D as an aid to understanding the operation. The encircled letter designations of the graphs are placed at points in the circuit where the signals they represent appear. A sixty Hz square wave of graph A is supplied by a source 140 to a 4017-type counter 142. This is allowed to count 0-5.

The 0 and 1 outputs are connected to an OR gate 144 that outputs a wave B that is in a high state during counts 0 and 1 to the base electrode of an NPN transistor 146 having its emitter connected to ground and its collector connected to a point of positive operation potential via a current limiting resistor 148 and an inductance coil 150 that are shunted by a diode 151. The inductance coil 150 is coupled in a manner well known, but not shown, so as to rotate the valve $v_6$ to the dotted-line position during periods $P_2$ and to permit it to return to its solid-line position during periods $P_1$.

The 0 count output of the counter 142, graph C, is also applied to trigger a multivibrator 152, type 14528, having a variable resistor 154, a capacitor 156 and a connection to ground as required. By varying the value of the resistor 154, the timing of positive pulses at the Q output shown in graph D can be adjusted. The purpose of this adjustment is to insure that the integrator 118 has a gain of unity when the stored sample gas is passing through the flame 88 during $T_i$. Some delay is generally required in order to allow for the time it takes for the top of the stored sample gas to move from the junction $J_6$ to the flame 88. The timing of corresponding inverted pulses, not shown, that appear at the $\overline{Q}$ output is the same as the positive pulses.

The inverted pulses, not shown, at the $\overline{Q}$ output of the multivibrator 152 are applied to the reset input R of an oscillator 158, type 555, and the pulses at the Q output are applied to the reset input R of a counter 160, type 4020, that serves to reduce the frequency of the oscillator 158 and provide a square wave output at its $Q_4$ terminal such as illustrated by the graph E. The frequency of these square waves can be adjusted by varying the frequency of the oscillator 158. For this purpose, a resistor 162, a variable resistor 164 and a capacitor 166 are connected as required. Note that the square waves start up a given time after the reset pulses on the Q and $\overline{Q}$ outputs of the delay multivibrator 152. The reset synchronizes the oscillator with the 60 Hz signal. The square waves of the graph E at the $Q_4$ output of the counter 160 are applied to the input of a 0-7 counter 168 that is reset by connection of its R input to the Q output of the delay multivibrator 152. The counter uses its enable (EN) input to stop at 7 until reset. The counter 168 controls the synchronous detector as well as the sample-and-hold circuit.

The FET 126 coupled to the integrating operational amplifier 118 is usually conducting so that the output of the amplifier is at ground potential and the amplifier has zero gain. The FET 130 is also normally conducting so that the inverter amplifier 122 would, if it were not for the conduction of the FET 126, make the gain of the amplifier 118 $-\frac{1}{4}$. The 0 and 7 count outputs of the counter 168 are respectively connected to the inputs of a NOR gate 170 so that it outputs a low state pulse shown in graph F to the gate of the FET 126 during these counts. During the counts 1-6, the output of the NOR gate 170 goes high so as to cause the FET 126 to cease conducting and permit the gain of the integrating amplifier 118 to go to $-\frac{1}{4}$ except when the inverting amplifier 122 is disconnected by application of the 3 count output of the counter 168 to the gate of the FET 130. During this count, the gain of the integrating amplifier 118 is unity. As a result of the operation of the FETs 126 and 130 just described, the gain of the integrating amplifier 118 changes as indicated by graph G. If the delay provided by the multivibrator 152 is correct, the unity gain of the amplifier 118 will coincide with the time when the stored sample gas is flowing through the flame 88 and producing an output signal at 96 such as illustrated in the graph H. The properly integrated value of the output signal will therefore appear at the output of the integrating amplifier 118. Slow variations in baseline values appearing at the output 76 will have nearly the same value during the variation of the gain of the integrating amplifier 118 from zero so as to yield an integrated value of zero.

Control of the sample-and-hold circuit is effected as follows. One period before the gain of the integrating amplifier 118 returns to zero, a sharp pulse shown in graph I is applied to the gate of the FET 134 so as to cause it to conduct momentarily and charge the capacitor 136 to the integrated value then at the output of the integrating amplifier 118. The pulses in the graph I may be produced by connecting the 6 count output of the counter 168 to a single-shot multivibrator 172 and applying its Q output to the gate of the FET 134. A resistor 174 and a capacitor 176 are connected as required.

What is claimed is:

1. Apparatus including a detector for deriving from a continuous flow of sample fluid an output signal corresponding to the value of a given characteristic of the fluid applied to the detector in such manner as to substantially eliminate the effect of low frequency drift in the output signal of the detector and increase the signal-to-noise ratio, comprising a detector having a fluid input and an electrical output and for producing at said output a signal corresponding to the value of a given characteristic of fluid applied to its fluid input, means defining a storage volume, means for connecting a source of a flow of sample fluid, when present, to said storage volume during first periods of time, means for conducting reference fluid from a source, when present, to the fluid input of said detector at an increased rate during said first periods of time, means for conducting fluid stored in said storage volume to the fluid input of said detector at an increased rate during second periods of time that are interleaved with the first, and synchronous demodulating means coupled to the electrical output of said detector for deriving an output signal corresponding to the peak-to-peak amplitude of an electrical signal appearing at the output of said detector.

2. Apparatus for producing an electrical signal corresponding to the value of a given characteristic of a sample chemical fluid flowing from a source in such manner as to improve the signal-to-noise ratio while virtually eliminating the effect of slow drift in the output of the detector, comprising a detector having a fluid input to which fluid may be applied and an electrical output at which it produces a signal corresponding to the value of a given characteristic of fluid that has entered its fluid input, a first input port coupled to said source, when present, so as to receive the flow of sample fluid, there being a connection between said first input port and said detector fluid input so that fluid can be made to flow between them, a second input port to which a source of reference fluid may be coupled, when present, there being a connection between said second input port and said fluid input of said detector so that fluid can be made to flow between them, means including storage means coupled to said first input port and said fluid input of said detector for modulating the flow of sample fluid entering said fluid input such that it has a minimum value during first spaced periods of time and a maximum value during second periods of time that are interleaved with the first, means coupled to said second input port for modulating the flow of reference fluid to it from a source of reference fluid, when present, so that the flow of reference fluid has a maximum value when the flow of sample fluid to said fluid input of said detector is minimum and a minimum value when the flow of sample fluid to said fluid input of said detector is maximum, and synchronous demodulating means coupled to said electrical output of said detector for deriving an electrical signal representing the peak-to-peak value of the signals appearing at the electrical output of said detector.

3. Apparatus as set forth in claim 2 wherein the means for modulating the flow of sample fluid is comprised of
   means defining a storage volume having an input and an output, said output being coupled to said fluid input of said detector, said input being coupled to said first input port,
   a tube having one end communicating with said first input port,
   a valve having an input and an output, said input being connected to a source of reference fluid, when present, and
   valve control means for connecting the output of said valve to the other end of said tube during said second periods and disconnecting it therefrom during said first periods.

4. Apparatus as set forth in claim 2 wherein said means for modulating the flow of reference fluid is comprised of
   a tube having one end in communication with the fluid input of said detector,
   a valve having an input and an output, said input being connected to a source of reference fluid, when present, and
   valve control means for connecting said output of said valve to the other end of said tube during said first periods and disconnecting it therefrom during said second periods.

5. Apparatus as set forth in claim 2 wherein said means for modulating the flow of sample fluid is comprised of
   means defining a storage volume having an input and an output, said output being coupled to said fluid input of said detector,
   valve means having an input and an output, said output being coupled to the input of said storage means, and
   control means for connecting said input of said valve means to said first input port during said first periods of time and for disconnecting it therefrom during said second periods of time.

6. Apparatus as set forth in claim 2 wherein said means for modulating the flow of reference gas between said second input port and said fluid input of said detector is comprised of valve means having an input and an output, said output being coupled to said input of said storage volume, and control means for connecting said input of said valve means to said second input port during said second periods and for disconnecting it therefrom during said first periods.

7. Apparatus as set forth in claim 2 wherein said detector is responsive to the mass flow rate of sample fluid passing through it and wherein said means for modulating the flow of sample fluid operates such that said first periods of time are much longer than said second periods of time and wherein said demodulating means responds to the sample flow through it during said second periods of time and an equal gain signal product measured during the rest of the time or a portion thereof.

8. Detector apparatus comprising, in combination,
   a flame ionization detector having a gas input and an electrical output,
   a source of continuous flow of sample gas to be analyzed,
   means defining a storage volume having an input coupled to said source of sample gas and an output coupled to said gas input of said detector,
   a first tube having one end communicating with said gas input of said detector,
   a second tube having one end communicating with said storage volume at a point near its gas input,
   a source of flammable gas under pressure,
   a valve having an input communicating with said source of flammable gas, and an output,
   means for connecting said output of said valve to the other end of said first tube during first spaced periods of time and with the other end of said second tube during second periods of time that are interleaved with said first periods of time, said first periods of time being longer than said second periods of time, and
   synchronous demodulator means coupled to the electrical output of said detector for deriving an electrical signal corresponding to the difference between the electrical signal produced during said second periods of time and a portion of the electrical signal produced during said second periods of time whereby the signal energy corresponding to the flow of sample gas through said detector is maximized and the signal energy resulting from noise is minimized and the effects of slow variation in the baseline value of the detector are virtually eliminated.

9. Detector apparatus comprising, in combination,
   a flame ionization detector having a gas input and an electrical output,
   a source of continuous flow of sample gas to be analyzed,
   means defining a storage volume having an output connected to the gas input of said detector, said storage volume also having an input,
   a source of flammable gas,
   a source of a continuous flow of sample gas to be analyzed,
   valve means for coupling said source of sample gas to said input of said storage volume during spaced first periods of time, and for coupling said source of flammable gas to said input of said storage means and blocking flow from said source of sample gas during second periods of time that are shorter than said first periods of time and interleaved therewith, and synchronous demodulator means coupled to the electrical output of said detector for deriving an electrical signal corresponding to the difference between the electrical signal produced during said second periods of time and a portion of the electrical signal produced during said second periods of time whereby the signal energy corresponding to the flow of sample gas through said detector is maximized and the signal energy resulting from noise is minimized and the effects of slow variation in the baseline value of the detector are virtually eliminated.

10. Detector apparatus comprising, in combination, a thermal conductivity detector having a gas input and an electrical output, a source of a continuous flow of sample gas to be analyzed, means defining a storage volume having an input coupled to said source of sample gas and an output coupled to said gas input of said detector, a first tube having an end in communication with said gas input of said detector, a second tube having one end in communication with said storage volume at a point near its gas input, a source of reference gas under pressure, a valve having an input communicating with said source of reference gas, and an output, means for connecting said output of said valve to the other end of said first tube during first spaced periods of time and with the other end of said second tube during second periods of time that are interleaved with the first periods and of equal duration, and synchronous demodulator means coupled to the electrical output of said detector for deriving the difference between the amplitude of the signal produced thereat during said first periods of time and the amplitude of the signal during said second periods of time.

* * * * *

UNITED STATES PATENT AND TRADEMARK OFFICE
CERTIFICATE OF CORRECTION

PATENT NO. : 4,316,381
DATED : February 23, 1982
INVENTOR(S) : Terry A. Woodruff It is certified that error appears in the above-identified patent and that said Letters Patent are hereby corrected as shown below:

| | | |
|---|---|---|
| Column 5 | line 41 | "reflkct" should read -- reflect -- |
| Column 6 | line 11 | "from" should read -- form -- |
| Column 8 | line 8 | "solide" should read -- solid -- |
| Column 11 | line 12 | "$V_s < P_2(F_c + F_h)$" should read -- $V_s > P_2(F_c - F_h)$ -- |

Signed and Sealed this

Fifteenth Day of June 1982

[SEAL]

Attest:

GERALD J. MOSSINGHOFF

Attesting Officer — Commissioner of Patents and Trademarks